(12) United States Patent
Heindl et al.

(10) Patent No.: US 10,839,045 B2
(45) Date of Patent: Nov. 17, 2020

(54) METHOD AND SYSTEM FOR SUPPORTING A MEDICAL BRAIN MAPPING PROCEDURE

(71) Applicant: Brainlab AG, Munich (DE)

(72) Inventors: Nadja Heindl, Munich (DE); Uli Mezger, Heimstetten (DE)

(73) Assignee: Brainlab AG, Munich (DE)

( * ) Notice: Subject to any disclaimer, the term of this patent is extended or adjusted under 35 U.S.C. 154(b) by 1026 days.

(21) Appl. No.: 15/116,603

(22) PCT Filed: Apr. 3, 2014

(86) PCT No.: PCT/EP2014/056673
§ 371 (c)(1),
(2) Date: Aug. 4, 2016

(87) PCT Pub. No.: WO2015/149854
PCT Pub. Date: Oct. 8, 2015

(65) Prior Publication Data
US 2017/0193158 A1 Jul. 6, 2017

(51) Int. Cl.
*A61B 6/00* (2006.01)
*G06F 19/00* (2018.01)
*A61B 5/00* (2006.01)
*A61B 90/00* (2016.01)

(52) U.S. Cl.
CPC .......... *G06F 19/321* (2013.01); *A61B 5/0042* (2013.01); *A61B 5/0082* (2013.01); *A61B 5/4064* (2013.01); *A61B 5/4887* (2013.01); *A61B 5/743* (2013.01); *A61B 90/37* (2016.02)

(58) Field of Classification Search
None
See application file for complete search history.

(56) References Cited

U.S. PATENT DOCUMENTS

| | | | |
|---|---|---|---|
| 6,196,226 B1 | 3/2001 | Hochman et al. | |
| 6,240,308 B1 | 5/2001 | Hardy et al. | |
| 2006/0293557 A1 | 12/2006 | Chuanggui | |
| 2008/0269602 A1* | 10/2008 | Csavoy | A61B 90/18 600/426 |
| 2009/0220136 A1* | 9/2009 | Bova | A61B 6/5247 382/131 |

(Continued)

FOREIGN PATENT DOCUMENTS

| | | |
|---|---|---|
| GB | 1431653 | 4/1976 |
| WO | 2012/0164173 A2 | 12/2012 |

(Continued)

OTHER PUBLICATIONS

International Search Report, PCT/EP2014/056673, dated Jan. 21, 2015,, 4 pages.

(Continued)

*Primary Examiner* — Joel F Brutus
(74) *Attorney, Agent, or Firm* — Tucker Ellis LLP

(57) ABSTRACT

A data processing method performed by a computer for supporting a medical brain mapping procedure, comprising the steps of receiving a microscope image of a patient's cortex and superimposing stimulation response marks onto the microscope image, wherein a stimulation response mark indicates the patient's response to an electrical stimulation of the cortex by a stimulation probe at a position associated with the stimulation response mark.

15 Claims, 3 Drawing Sheets

(56) References Cited

U.S. PATENT DOCUMENTS

Figure 1:
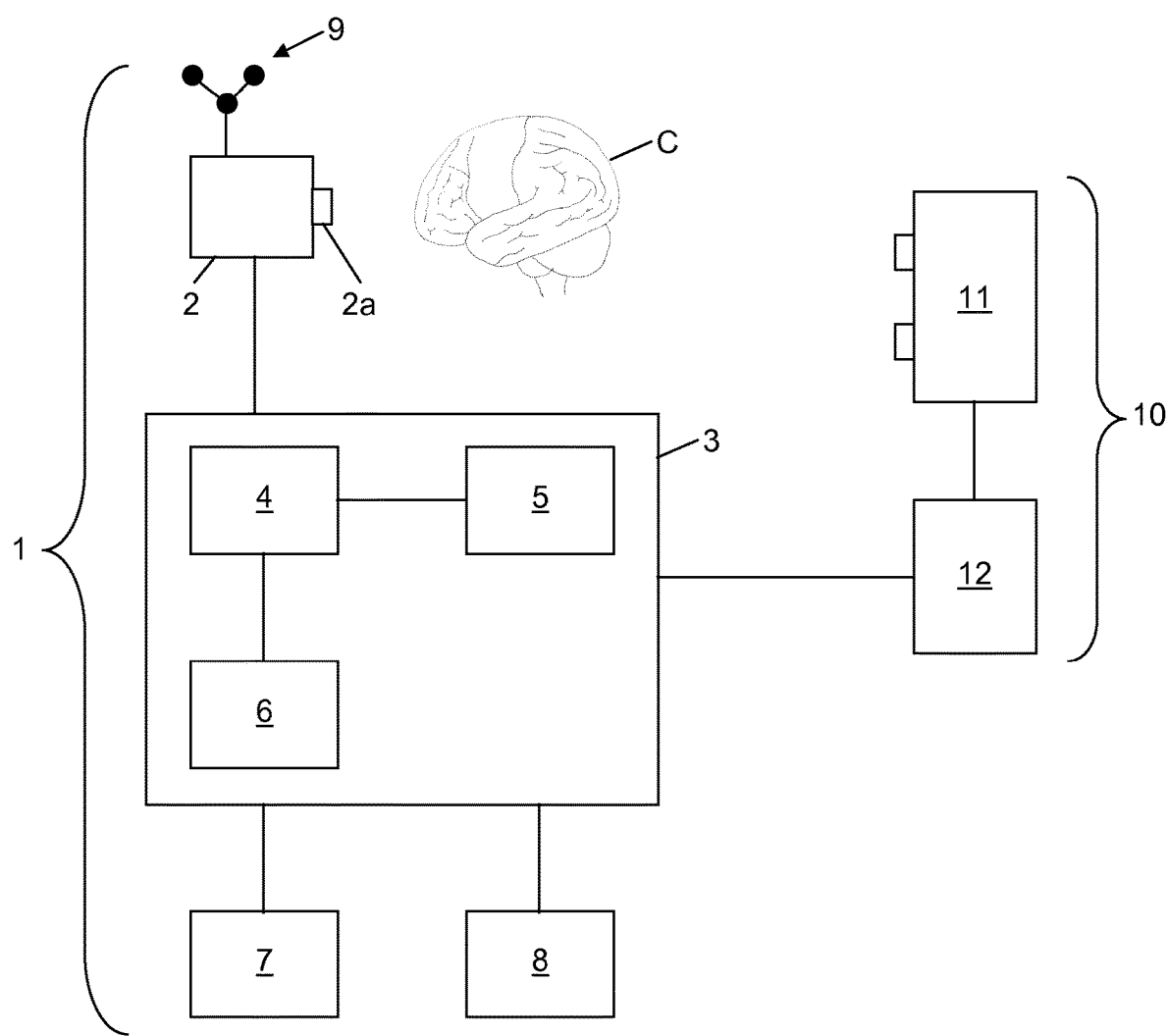

| | | | |
|---|---|---|---|
| 2011/0199532 A1 | 8/2011 | Jin | |
| 2013/0176336 A1* | 7/2013 | Hannula | A61B 5/0042 345/633 |
| 2014/0200633 A1* | 7/2014 | Moffitt | A61N 1/37235 607/62 |

FOREIGN PATENT DOCUMENTS

| | | | |
|---|---|---|---|
| WO | 2012164173 A2 | 12/2012 | |
| WO | 2014117805 A1 | 8/2014 | |

OTHER PUBLICATIONS

Oehring, Susann, Thesis, Navigationsgestützte Aufnahme und Wiedergabe von Endoskopiebildern in der Nasennebenhöhlenchirurgie, Technische Universität Ilmenau, Apr. 26, 2006.

European Search Report for corresponding European Application No. 18201230.2-1132, dated Feb. 22, 2019.

International Search Report, PCT/EP2014/055133, dated Nov. 17, 2014, 3 pages.

* cited by examiner

METHOD AND SYSTEM FOR SUPPORTING A MEDICAL BRAIN MAPPING PROCEDURE

RELATED APPLICATION DATA

This application is a national phase application of International Application No. PCT/EP2014/056673 filed Apr. 3, 2014 published in the English language.

The present application relates to a data processing method, a computer program and a system for supporting a medical brain mapping procedure.

Brain surgery is a difficult task because an erroneous incision could severely impair the brain's capabilities. It is therefore essential to gather information about functional areas of the brain. This results in a "safe resection map" which indicates areas which are safe to resect. Cortical areas therefore have to be divided into areas to be avoided (eloquent areas) and areas which can be resected (non-eloquent areas). An eloquent area, or eloquent cortex, is an area of the cortex which, if removed, leads to a loss of sensory processing or linguistic ability or to minor or major paralysis. A standard approach for segmenting the cortex into eloquent and not-eloquent areas is referred to as brain mapping.

In the conventional brain mapping procedure, paper marks—i.e. small pieces of paper—are distributed over the exposed cortex. A surgeon then uses a stimulation probe to stimulate the brain at the positions marked by the paper marks. The behaviour of the patient is then monitored in order to determine whether the stimulated area is an eloquent area or not.

The disadvantage of this approach is that the stimulation might cause a seizure, which is then typically stopped using ice water. However, using ice water washes the paper marks away, such that the stimulation results obtained hitherto are lost and the process has to be repeated from the beginning.

The aim of the present invention is to support a medical brain mapping procedure in order to avoid the problems which arise in the prior art.

The present invention relates to a data processing method performed by a computer for supporting a medical brain mapping procedure. The method comprises the steps of receiving a microscope image of a patient's cortex and superimposing stimulation response marks onto the microscope image. A stimulation response mark indicates the patient's response to an electrical stimulation of the cortex by a stimulation probe in an area associated with the stimulation response mark. In this document, an area on the cortex which is probed using a stimulation probe, i.e. an area which is stimulated, is referred to as a "probed area". The microscope image is preferably a video image, i.e. a sequence of images.

Modern microscopes for medical use supplement an optical system with a digital system used for digitising the image which is captured using the optical system of the microscope. The microscope then displays the digitised image on a display device or provides the image to an external display device connected to the microscope. In accordance with the present invention, the digitised image, which is also referred to as the microscope image, is enhanced by adding stimulation response marks. In the superimposing step, the stimulation response marks are added to the microscope image in an opaque or partly transparent manner. Since the stimulation response marks are virtual marks in the microscope image, unlike the paper marks used hitherto, they are not washed away if the patient has a seizure which then has to be stopped. The stimulation response mark indicates the patient's response, in particular whether or not stimulating an area associated with the stimulation response mark identifies the probed area as belonging to an eloquent area. The stimulation response mark can optionally indicate additional information, such as the properties of the stimulation, including parameters such as the stimulation voltage or stimulation current. The stimulation response mark can also optionally indicate whether the area corresponding to the stimulation response mark has been probed yet or not.

The probed area exhibits a position in three-dimensional space. The position of a stimulation response mark in the microscope image, which is also referred to as a "response mark position", is a position in the virtual space of the microscope image. If the microscope image is a three-dimensional image which virtually represents the three-dimensional surface of the cortex, then the response mark position relative to this three-dimensional representation of the surface lies within the virtual representation of the probed area in the microscope image. If the microscope image is a two-dimensional image, in particular a projection of the cortex into an imaging plane of the microscope, then the response mark position preferably lies within an area of the microscope image which is the projection of the probed area into the imaging plane. In other words, the stimulation response marks are located at positions in the microscope image which show the respective probed areas.

In one embodiment, the method comprises the steps of recognising physical marks, in particular paper marks, on the cortex in the microscope image and positioning the stimulation response marks accordingly. In other words, the response mark positions preferably match the positions of the physical marks in the microscope image. In this embodiment, the manually placed physical marks can thus be converted into (virtual) stimulation response marks, such that the physical marks can be removed once the stimulation response marks have been positioned. The surgeon's experience in placing physical marks can thus be utilised, while manually placing the stimulation response marks in the microscope image may be an unacceptable burden to the surgeon. A mark, such as a physical mark or a stimulation response mark, typically extends in at least two dimensions, in which case the position of a mark is preferably the centre of the mark.

In another embodiment, the method comprises the step of automatically defining the positions of the stimulation response marks. This means that the stimulation response marks are automatically placed in the microscope image of the cortex. In the case of this step, the number of stimulation response marks to be placed is preferably received as an input parameter. Another optional input parameter is boundary data which represent a boundary in the microscope image within which the stimulation response marks are positioned. The boundary data are preferably inputted by the surgeon. Areas in the microscope image which correspond to areas of the cortex which are not of interest are then not provided with stimulation response marks.

In one particular implementation of this embodiment, the positions of the stimulation response marks are determined from an atlas of the cortex. The atlas of the cortex can comprise default areas to be probed, i.e. so-called default probed areas. The atlas is then matched to the cortex as it is imaged by the microscope, wherein the default probed areas are adapted together with the atlas. Response mark positions corresponding to the adapted default probed areas are then selected from the matched atlas to form the stimulation response marks in the microscope image.

In one embodiment of the invention, the method also comprises the step of superimposing positioning marks onto the microscope image. The positioning marks represent—i.e. exhibit the shape of—particular structures of the cortex, such as sulci, in the microscope image of the cortex. In one preferred embodiment, a positioning mark is a line which traces out, i.e. delineates the contour of, a sulcus of the cortex as shown in the microscope image. The positioning marks can be used to determine whether or not the microscope has moved relative to the cortex, in which case the electrical stimulation marks probably no longer correspond to the probed areas on the cortex. If the microscope has moved, the positioning marks no longer coincide with the structures in the microscope image. Additionally or alternatively, the positioning marks can be used to re-position the microscope after it has been moved, such that the positioning marks again coincide with the structures in the microscope image. Once this is the case, the stimulation response marks again correctly represent the probed locations on the cortex.

It should be noted that the expression "movement of the microscope" as used in this document means in particular a movement of the part of the microscope which is used to obtain the microscope image. In particular, movement of the microscope means a rotation and/or a translation of the input lens of the microscope. The input lens of a microscope is a lens through which light enters the optical system of the microscope.

In one embodiment of the invention, the method comprises the step of determining the probed stimulation response mark from the position of the stimulation probe in the microscope image. In this document, the expression "probed stimulation response mark" is understood to mean the stimulation response mark which corresponds to the area on the cortex which is being stimulated, and the expression "position of the stimulation probe" in particular means the position of the tip of the stimulation probe which is brought into contact with the cortex. The position of the stimulation probe in the microscope image is in particular determined by image processing in which the microscope image could be compared with a reference image of the stimulation probe, or at least the tip of the stimulation probe, and/or movement could be detected in temporally consecutive microscope images in order to determine the position of the stimulation probe. If the position of the stimulation probe in the microscope image corresponds to and preferably matches the position of a stimulation response mark, then said stimulation response mark is determined as the probed stimulation response mark. In this context, the term "matches" means that it is within a predetermined distance such as for example 2, 3, 5 or 10 pixels.

The position of the stimulation probe in the microscope image is preferably only compared to the position of a stimulation response mark if the position of the stimulation probe is constant in a predetermined number of temporally consecutive microscope images, such as for example 5, 10, 20 or 50 temporally consecutive microscope images, wherein the term "constant" preferably means within a predetermined distance such as for example 2, 3, 5 or 10 pixels. If an area on the cortex is stimulated, the stimulation probe is held in place for a while. This means that there is typically no stimulation while the stimulation probe is being moved, hence if, during the movement of the stimulation probe, its position within the microscope image coincides with the position of a stimulation response mark for less than the predetermined number of images, then this is not considered to constitute the stimulation of an area corresponding to the stimulation response mark.

In another embodiment of the invention, the method also comprises the step of determining the probed stimulation response mark from the position of the stimulation probe, wherein the position of the stimulation probe is determined by tracking a marker device attached to the stimulation probe. The stimulation probe and its marker device are registered, such that the position of the stimulation probe and in particular the position of the tip of the stimulation probe is known relative to the marker device. By tracking the marker device in physical space, the position of the stimulation probe can be determined using a medical navigation system.

In one implementation, the position of the stimulation probe is determined relative to the cortex, hence the probed area on the cortex is known. The stimulation response mark which is superimposed onto the microscope image and corresponds to the probed area can then be determined. This allows the stimulation response mark which is associated with the probed area to be unambiguously determined.

In another implementation, the position of the stimulation probe is determined relative to the microscope. The position of the stimulation probe in the microscope image can then be calculated by taking into account the known imaging properties of the microscope. The probed stimulation response mark is then the stimulation response mark at the position of the stimulation probe in the microscope image.

In one implementation of this embodiment, the electrical stimulation is automatically initiated when the tip of the stimulation probe is determined to be in contact with the cortex within an area corresponding to a stimulation response mark and in particular to a stimulation response mark which has not yet been probed.

In one embodiment of the invention, the method also comprises the steps of: acquiring stimulation response information which represents the patient's response to the stimulation; and setting visual properties of the corresponding stimulation response mark in accordance with the stimulation response information. The stimulation response mark can for example be assigned a first colour and/or a first shape if the stimulation response information indicates that the probed area corresponding to the stimulation response mark is an eloquent area, and can be assigned a second colour and/or a second shape if the stimulation response information indicates that the probed area corresponding to the stimulation response mark is a non-eloquent area. The stimulation response mark could also be assigned a third colour and/or a third shape if the corresponding area on the cortex has not yet been probed.

One way of acquiring the stimulation response information involves detecting a movement pattern performed by the stimulation probe. In this case, there would in particular be two predetermined movement patterns, one representing an eloquent area and the other representing a non-eloquent area. The movement pattern could for example be identified by performing image processing on temporally consecutive microscope images and/or by tracking a marker device attached to the stimulation probe. In this implementation, the surgeon does not need to operate additional input means, such as for example an input unit of the computer, and therefore does not need to remove their hands from the instruments which they are using to stimulate the cortex.

Another way of acquiring the stimulation response information involves receiving a stimulation response signal, which represents the stimulation response information, from a transmitter attached to the stimulation probe or the microscope. The transmitter can transmit the stimulation response signal via a wire connection or wirelessly. The transmitter preferably comprises an input unit, such as a button, for receiving the stimulation response information from the surgeon, which is then transmitted in the stimulation response signal. The input unit can for example be pressed once and/or briefly for an eloquent area, and twice and/or longer for a non-eloquent area, or vice versa. The transmitter can for example be a SmartClip such as is offered by the applicant of the present application.

In one embodiment, the method also comprises the step of determining the position of the microscope. As already outlined above, the expression "position of the microscope" in particular means the position of the optical unit of the microscope in three-dimensional space. There are numerous ways of utilising the position of the microscope, any two or more of which can also be combined.

In accordance with a first option, the positions of the stimulation response marks in the microscope image can be adapted in accordance with a movement of the microscope, i.e. a change in the position of the microscope. In particular, the positions of the stimulation response marks are adapted such that they correspond to the actual positions of the probed areas on the cortex in the microscope image. The position of the microscope relative to the cortex in particular is known, such that the projection of the probed areas on the cortex into the image plane can be calculated. The stimulation response marks are then placed at positions within the projected probed areas. The stimulation response marks will then correctly represent the probed areas even if the microscope is moved.

It should be noted that the positions of the stimulation response marks in the microscope image can also be adapted without determining the position of the microscope, in particular by using image analysis. In one such implementation, a microscope image taken at a first point in time and comprising the stimulation response marks is fused or matched to a microscope image taken at a second point in time which is later than the first point in time. This results in a transformation which is then applied to the position of the stimulation response marks in the first microscope image, thus approximating the position of the stimulation response marks in the second microscope image. Suitable 2D image registration algorithms for this purpose are known to the person skilled in the art.

In accordance with a second option, the position of the microscope can be used to determine the position of the stimulation probe relative to the microscope. The probed stimulation response mark can then be determined, as already explained above, from the relative position between the microscope and the stimulation probe.

In accordance with a third option, a warning can be triggered if the microscope is moved, i.e. if the position of the microscope changes. If the positions of the stimulation response marks in the microscope image are not adapted as explained above with respect to the first option, then the warning indicates that the positions of the stimulation response marks in the microscope image no longer correctly represent the probed areas.

In accordance with a fourth option, the position of the microscope relative to the imaged cortex can be used to register the atlas of the cortex to the microscope image. Some algorithms for registering a three-dimensional image, such as an atlas, to a two-dimensional image require an initial relative position between the three-dimensional image and the two-dimensional image, which is then refined during the registration process. This initial relative position can be determined from the relative position between the microscope and the cortex.

In one embodiment, the method also comprises the step of superimposing a viewing direction indicator, which represents the viewing direction of the microscope, onto the microscope image, wherein the "viewing direction" of the microscope means the viewing direction relative to or onto the patient. In one implementation, the viewing direction indicator comprises letters indicating anatomical directions. If, for example, the microscope images the patient from the patient's left side, then the letter A at the left-hand border of the microscope image can indicate the anterior direction, the letter P at the right-hand border of the microscope image can indicate the posterior direction, the letter H at the upper border of the microscope image can indicate the cranial direction (towards the head) and the letter F can indicate the caudal direction (towards the feet). In another implementation, an icon representing a (stylised) human body is used as the viewing direction indicator, wherein the viewing direction of the icon corresponds to the viewing direction of the microscope onto the patient.

In one embodiment, the method also comprises the step of indicating safety zones in the microscope image around the stimulation response marks. A safety zone indicates a resectable area of the cortex in which a resection can be performed if the corresponding stimulation response mark indicates a non-eloquent area. A safety zone is for example a circular area which is preferably centred over the stimulation response mark. The radius of the circular area preferably correlates with the intensity of the stimulation, such as the stimulation voltage or stimulation current. Additionally or alternatively, the method comprises the step of indicating prohibition zones in the microscope image. A prohibition zone comprises the position of a corresponding stimulation response mark around the stimulation response marks. A prohibition zone indicates a prohibited area of the cortex in which resection must not be performed if the corresponding stimulation response mark belongs to an eloquent area. A prohibition zone can be at least one circular area, can be centred over a corresponding stimulation response mark and can vary in size depending on the stimulation intensity, as explained above with respect to the safety zones, wherein "indicating" a zone in the microscope image means highlighting an area in the microscope image, for example by superimposing a mark in an opaque or (semi-)transparent manner.

The present invention also relates to a computer program which, when running on a computer, causes the computer to perform the method as described above and/or to a program storage medium on which the program is stored, in particular in a non-transitory form.

The present invention also relates to a system for supporting a medical brain mapping procedure, comprising a computer on which the aforementioned program is stored and/or run.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which in particular comprises technical, in particular tangible components, in particular mechanical and/or electronic components. Any device mentioned as such in this document is a technical and in particular tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is in particular part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block X-ray radiation. To this end, the marker can be provided with a surface which has corresponding reflective properties or can be made of metal in order to block the X-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is in particular known to a navigation system and is for example stored in a computer of the navigation system.

An atlas typically consists of a plurality of generic models of objects, wherein the generic models of the objects together form a complex structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

The method in accordance with the invention is in particular a data processing method. The data processing method is preferably performed using technical means, in particular a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the World Wide Web (WWW) and located in a so-called cloud of computers which are all connected to the World Wide Web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (or World Wide Web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or which are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer.

In particular, the invention does not involve or in particular comprise or encompass an invasive step which would represent a substantial physical interference with the body requiring professional medical expertise to be carried out and entailing a substantial health risk even when carried out with the required professional care and expertise. In particular, the invention does not involve or in particular comprise or encompass any surgical or therapeutic activity. For this reason alone, no surgical or therapeutic activity and in particular no surgical or therapeutic step is necessitated or implied by carrying out the invention.

In particular, the method according to the present invention does not comprise the steps of exposing and/or stimulating the cortex, but rather merely involves processing data acquired during a brain mapping procedure. The steps of exposing and/or stimulating the cortex is/are carried out during the brain mapping procedure anyway, while the method according to the present invention merely supports and/or enhances the brain mapping procedure. In other words, the present invention does not require any surgical steps which are not already carried out in the prior art.

Figure 2:
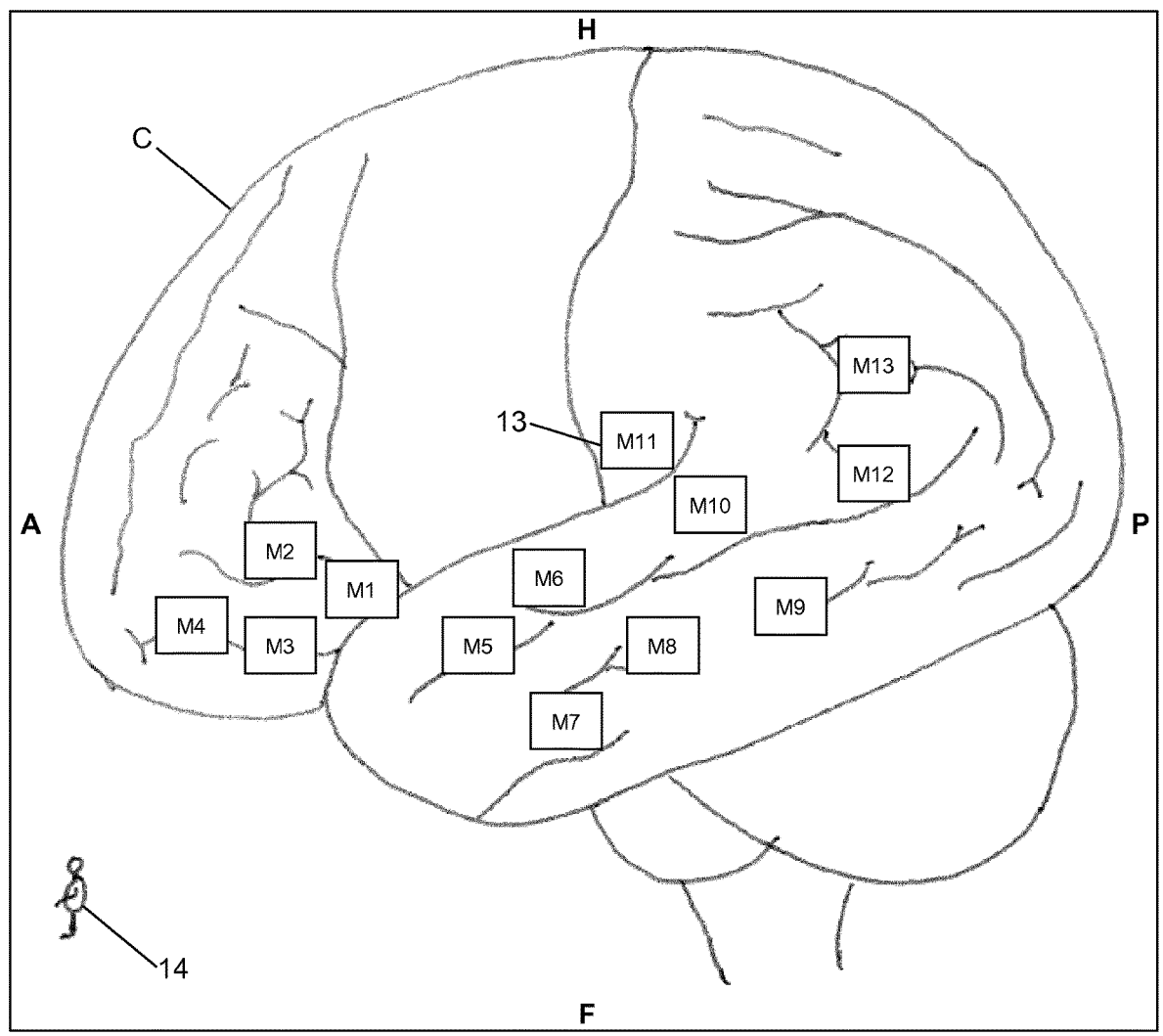

In the following, the invention is described with reference to the enclosed figures which represent preferred embodiments of the invention. The scope of the invention is not however limited to the specific features disclosed in the figures. The figures show:

FIG. 1 a system in accordance with the present invention;

FIG. 2 a microscope image of a cortex with physical marks; and

Figure 3:
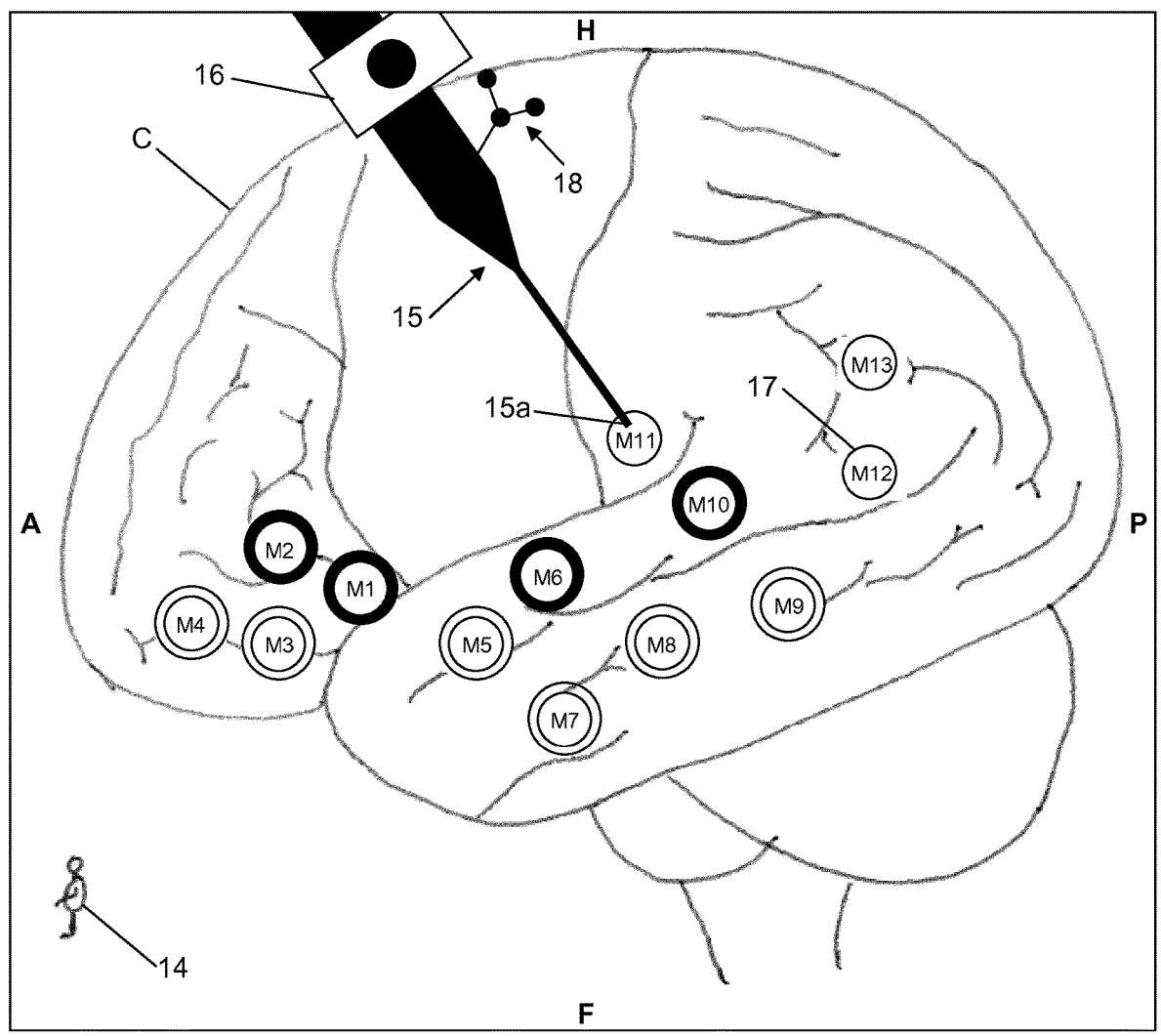

FIG. 3 the microscope image of FIG. 2 with superimposed stimulation response marks.

FIG. 1 schematically shows a system in accordance with the present invention, comprising a microscope 1. The microscope 1 comprises a microscope camera 2 which is connected to a microscope computer 3. The microscope camera 2 comprises an input lens 2a through which light reflected by a cortex C, at which the microscope camera 2 is directed, enters the microscope camera 2. The microscope camera 2 comprises an optical system including the input lens 2a and a digitiser for digitising the optical image into a digital microscope image. In this embodiment, the image is a two-dimensional image which represents the projection of any object within the field of view of the microscope camera 2 into an image plane. The microscope image is a moving image, which means a video image or sequence of still images. The digital microscope image, referred to in the following simply as the microscope image, is provided to the microscope computer 3. A marker device 9 comprising three reflective marker spheres in a known geometrical relationship is attached to the microscope camera 2.

The microscope computer 3 comprises: a central processing unit 4 for carrying out any method steps disclosed herein; a memory 5 which stores program data embodying the method steps and/or data to be processed by the central processing unit 4; and an interface 6 which can exchange data with other apparatus, i.e. transmit data to and/or receive data from other apparatus, such as for example computers. The microscope 1 also comprises an input unit 7, such as a mouse device and/or a keyboard and/or a touch-sensitive interface, and an output unit 8, such as a monitor or flat screen, which are connected to the microscope computer 3.

FIG. 1 also shows a medical navigation system 10 comprising a stereoscopic camera 11 which is connected to a navigation system computer 12. The stereoscopic camera 11 is adapted to capture a three-dimensional image of a marker device, such as the marker device 9 attached to the microscope camera 2, in order to determine the position of the marker device and therefore the position of an object to which the marker device is attached. The navigation system computer 12 receives the stereoscopic image from the stereoscopic camera 11 and is adapted to process the three-dimensional image in order to determine the position of an imaged marker device. In the example shown in FIG. 1, the microscope computer 3 and the navigation system computer 12 are connected, such that they can exchange data. In particular, the navigation system computer 12 can transmit the position of the marker device 9 to the microscope computer 3. The structure of the navigation system computer 12 is essentially identical to the structure of the microscope computer 3. It should be noted that the microscope computer 3 and the navigation system computer 12 can also be integrated into a single computer.

FIG. 2 schematically shows a microscope image of the cortex C as captured using the microscope camera 2 and provided to the microscope computer 3. A plurality of physical marks 13, which in the present embodiment are formed by square pieces of paper bearing the consecutive numbers M1 to M13, are placed on the cortex C. Viewing direction indicators, which in the present case take the form of four letters and an icon 14, are superimposed onto the microscope image. The letters A, H, P and F indicate anatomical directions of the cortex C, such that they represent the viewing direction of the microscope 1 onto the cortex C. The icon 14 represents a human body as seen from the same viewing direction as the cortex C in the microscope image.

It should be noted that while the microscope image shown in FIG. 2 encompasses the whole cortex C, this is merely for illustrative purposes, and in most practical applications, only a part of the cortex C is exposed.

The microscope computer 3 receives and processes the microscope image. In particular, the central processing unit 4 detects the positions of the physical marks 13 and superimposes stimulation response marks 17 onto the microscope image at the positions of the physical marks 13. The physical marks 13 are then no longer required.

FIG. 3 shows the microscope image of FIG. 2 at a subsequent point in time at which the physical marks 13 are no longer present on the cortex C and the circular stimulation response marks 17 are superimposed onto the microscope image. Each individual physical mark 13 corresponds to exactly one of the stimulation response marks 17, and each individual stimulation response mark 17 corresponds to exactly one of the physical marks 13. In the state shown in FIG. 3, a stimulation probe 15 is used to electrically stimulate points or areas on the cortex C. The stimulation probe 15 and its components are shown schematically and not necessarily to scale in FIG. 3. The areas in which the cortex C is stimulated are referred to as probed areas. Each probed area corresponds to one of the stimulation response marks 17.

Instead of detecting physical marks 13 in the microscope image in order to determine the locations of the stimulation response marks 17, it is also possible to provide an atlas of the cortex C, wherein the atlas comprises areas to be stimulated. The atlas is then matched to the microscope image of the cortex C, for example using image fusion, wherein the areas to be stimulated are matched along with the atlas. Areas corresponding to the matched areas to be stimulated are then identified in the microscope image, for example by calculating the projection of the matched areas into the image plane. Stimulation response marks 17 are then located in each of the areas identified in the microscope image.

The stimulation probe 15 is provided with a stimulation probe tip 15a which stimulates the cortex C. Though not shown in detail in FIG. 3, the tip 15a is fork-shaped and comprises two electrodes for providing electrical stimulation. The tip can however also be non-bifurcated and comprise a single electrode. A transmitter 16 attached to the stimulation probe 15 transmits a stimulation response signal to the microscope computer 3. The stimulation response signal represents stimulation response information indicating whether the stimulated area has been identified as an eloquent area or a non-eloquent area. The central processing unit 4 adapts the visual properties of the stimulation response marks 17 in accordance with the stimulation response information.

If the stimulation response information indicates an eloquent area, a circular prohibition zone centred over the corresponding stimulation response mark 17 is superimposed onto the microscope image. In the embodiment shown in FIG. 3, the stimulation response marks bearing the numbers 1, 2, 6 and 10 correspond to eloquent areas and are therefore surrounded by a prohibition area which is indicated by a black circle. The stimulation response marks numbered 3, 4, 5, 7, 8 and 9 correspond to non-eloquent areas and are therefore surrounded by safety zones indicated by white circles in FIG. 3. The stimulation response marks bearing the numbers 12 and 13 have not yet been probed, as indicated by the fact that they are surrounded by neither a safety zone nor a prohibition zone. The area corresponding to the stimulation response mark bearing the number 11 is currently being stimulated.

Although the actual stimulation process is not part of the present invention, it shall now be described in more detail for the purpose of explaining the technical background. The stimulation probe tip 15a contacts the cortex C in an area to be stimulated, i.e. in a probed area. During and/or after the stimulation, the patient is monitored by a physician in order to determine whether or not the electrical stimulation has impaired the patient's sensory processing or linguistic ability. The physician operates the transmitter 16 on the stimulation probe 15 in accordance with the observed result and thus inputs the stimulation response information to the microscope computer 3. If the probed area is an eloquent area, the button on the transmitter is for example pressed once and/or briefly, and if the probed area is a non-eloquent area, the button on the transmitter 16 is for example pressed twice and/or longer.

The stimulation response mark to which the probed position corresponds is automatically determined by the microscope computer 3. In one embodiment, the central processing unit 4 applies an image analysis in order to locate the stimulation probe tip 15a within the microscope image. The central processing unit 4 then associates the stimulation response information with the stimulation response mark whose position corresponds to the position of the stimulation probe tip 15a in the microscope image. The position of the stimulation probe tip 15a corresponds to the position of a stimulation response mark if the distance between the stimulation probe tip 15a and the stimulation response mark 17 in the microscope image is below a predetermined threshold, such as for example 3, 5 or 10 pixels. Once the stimulation response information has been associated with a stimulation response mark 17, the visual properties of this stimulation response mark 17 can be changed in accordance with the stimulation response information.

In an alternative embodiment, the stimulation response mark which corresponds to the probed area is determined by tracking the position of the stimulation probe 15. In this case, a marker device 18 is attached to the stimulation probe 15, and the position of the stimulation probe tip 15a relative to the marker device 18 is known. The medical navigation system 10 detects the position of the marker device 18 attached to the stimulation probe 15 and transmits it to the microscope computer 3. The microscope computer 3 can then determine the position of the stimulation probe tip 15a from the position of the marker device 18 and the known geometrical relationship between the marker device 18 and the stimulation probe tip 15a. Alternatively, the navigation system computer 12 determines the position of the stimulation probe tip 15a and transmits it to the microscope computer 3 instead of or in addition to the position of the marker device 18 which is attached to the stimulation probe 15.

A position (of the stimulation probe tip 15a or the marker device 18 attached to the stimulation probe 15) can for example be given in an absolute co-ordinate system, a co-ordinate system associated with the cortex C or relative to the position of the marker device 9 which is attached to the microscope camera 2. If the position is given in an absolute co-ordinate system or a co-ordinate system of the cortex C, the central processing unit 4 calculates the probed area on the cortex C from the positions of the cortex C and the stimulation probe tip 15a and determines the stimulation response mark which is associated with this probed area. This in particular involves calculating the position of the probed area in the microscope image, in particular taking into account the viewing direction of the microscope camera 2 onto the cortex C. The stimulation response mark which is associated with the probed area can then be determined as already explained above with regard to image analysis.

If an atlas of the cortex C is provided in the microscope computer 3 and the positions of the stimulation response marks 17 in the microscope image have been determined from an atlas of the cortex C instead of by detecting the physical marks 13, then the area in the matched atlas which corresponds to the probed area is determined, and the stimulation response mark 17 which is associated with the probed area is the stimulation response mark 17 which is associated with the determined area of the atlas.

If the position is given relative to the microscope camera 2, then the central processing unit 4 can determine the position of the stimulation probe tip 15a in the microscope image on the basis of this relative position and the imaging properties of the microscope camera 2. The stimulation response mark which is associated with the position of the stimulation probe tip 15a, and therefore the position of the probed area on the cortex C, can then be determined as already explained above with regard to image analysis.

Instead of using the transmitter 16, it is also possible to analyse a movement pattern of the marker device 18 attached to the stimulation probe 15 in order to determine the stimulation response information. The movement pattern is in particular determined using the medical navigation system 10. In one example, the stimulation probe 15 or at least the marker device 18 attached to the stimulation probe 15 is moved in a circle if the probed area is observed to belong to an eloquent area; otherwise, it is moved along a line or a circular arc. The movement pattern is detected by the navigation system computer 12 and transformed into corresponding stimulation response information which is transmitted from the navigation system computer 12 to the microscope computer 3. Alternatively, the navigation system computer 12 only transmits the detected pattern to the microscope computer 3, and the central processing unit 4 then determines the stimulation response information in accordance with the movement pattern received.

In the embodiment described in the foregoing, the microscope camera 2 is static with respect to the cortex C, such that the image of the cortex C does not change. However, if the microscope camera 2 does move relative to the cortex C, the positions of the stimulation response marks 17 no longer correspond to the probed areas as shown in the microscope image. In one implementation of this embodiment, the medical navigation system 10 determines the position of the marker device 9 and therefore the position of the microscope camera 2 and transmits it to the microscope computer 3. The microscope computer 3 detects a movement of the microscope camera 2 and adapts the positions of the stimulation response marks 17 in the microscope image such that they again coincide with the probed areas as shown in the microscope image.

If the microscope camera 2 only moves parallel to the image plane, then the positions of the stimulation response marks 17 in the microscope image are shifted accordingly. If the microscope camera 2 is only shifted in a direction perpendicular to the image plane, then the positions of the stimulation response marks 17 are scaled in order to match the new size of the cortex in the microscope image.

If the viewing direction of the microscope camera 2 onto the cortex C changes, then the positions of the stimulation response marks 17 change in accordance with the distance between the corresponding probed areas and the microscope camera 2. In this case, the central processing unit 4 uses a three-dimensional model of the cortex C, such as the atlas of the cortex C, to calculate the projections of the probed areas into the image plane and therefore into the microscope image, in accordance with the viewing direction of the microscope camera 2 onto the cortex C.

The invention claimed is:

1. A data processing system for supporting a medical brain mapping procedure, comprising a computer having a processor configured to:
   receive a microscope image of a cortex of a patient, the microscope image captured by a microscope;
   superimpose stimulation response marks onto the microscope image; and
   identify a probed stimulation response mark based on determining, via image processing, a position of a stimulation probe in the microscope image with respect to a superimposed mark of the stimulation response marks, wherein the probed stimulation response mark indicates a response by the patient to an electrical stimulation of the cortex of the patient by the stimulation probe located at a position associated with the stimulation response mark.

2. A computer-implemented medical data processing method for supporting a medical brain mapping procedure, the method comprising:
   receiving a microscope image of a cortex of a patient, the microscope image captured by a microscope;
   superimposing stimulation response marks onto the microscope image; and
   identifying a probed stimulation response mark based on determining, via image processing, a position of a stimulation probe in the microscope image with respect to a superimposed mark of the stimulation response marks, wherein the probed stimulation response mark indicates a response by the patient to an electrical stimulation of the cortex of the patient by the stimulation probe located at a position associated with the stimulation response mark.

3. The computer-implemented medical data processing method according to claim 2, further comprising:
   recognising physical marks on the cortex of the patient in the microscope image; and
   positioning the stimulation response marks based on the physical marks recognized in the microscope image.

4. The computer-implemented medical data processing method according to claim 2, further comprising:
   automatically defining positions of the stimulation response marks.

5. The computer-implemented medical data processing method according to claim 4, wherein positions of the stimulation response marks are determined from an atlas of the cortex of the patient.

6. The computer-implemented medical data processing method according to claim 2, further comprising:
   superimposing positioning marks onto the microscope image.

7. The computer-implemented medical data processing method according to claim 2, further comprising:
   determining the probed stimulation response mark from the position of the stimulation probe relative to the cortex or the microscope, wherein the position of the stimulation probe is determined by tracking a marker device attached to the stimulation probe.

8. The computer-implemented medical data processing method according to claim 2, further comprising:
   acquiring stimulation response information that represents the response by the patient to the electrical stimulation of the cortex of the patient; and
   setting visual properties of a corresponding stimulation response mark in accordance with the stimulation response information.

9. The computer-implemented medical data processing method according to claim 8, wherein acquiring the stimulation response information involves detecting a movement pattern performed by the stimulation probe.

10. The computer-implemented medical data processing method according to claim 8, wherein acquiring the stimulation response information involves receiving a stimulation response signal, which represents the stimulation response information, from a transmitter attached to the stimulation probe or the microscope.

11. The computer-implemented medical data processing method according to claim 2, further comprising:
    determining a position of the microscope.

12. The computer-implemented medical data processing method according to claim 2, further comprising:
 adapting positions of the stimulation response marks in the microscope image in a condition that the microscope is moved relative to the cortex of the patient.

13. The computer-implemented medical data processing method according to claim 2, further comprising:
 superimposing a viewing direction indicator, which represents a viewing direction of the microscope, onto the microscope image.

14. A non-transitory computer-readable program storage medium storing a computer program for supporting a medical brain mapping procedure, which, when executed on a processor of a computer, causes the processor to:
 receive a microscope image of cortex of a patient, the microscope image captured by a microscope;
 superimpose stimulation response marks onto the microscope image; and
 identify a probed stimulation response mark based on determining, via image processing, a position of a stimulation probe in the microscope image with respect to a superimposed mark of the stimulation response marks, wherein the probed stimulation response mark indicates a response by the patient to an electrical stimulation of the cortex of the patient by the stimulation probe located at a position associated with the stimulation response mark.

15. A computer comprising the non-transitory computer-readable program storage medium according to claim 14.

\* \* \* \* \*